United States Patent
Groskopf et al.

(10) Patent No.: US 11,547,810 B2
(45) Date of Patent: Jan. 10, 2023

(54) DRUG DELIVERY DEVICE FOR DRUG SUSPENSIONS

(71) Applicant: Becton, Dickinson and Company, Franklin Lakes, NJ (US)

(72) Inventors: Roger Groskopf, Saddle Brook, NJ (US); Behzad D. Mottahed, Upper Montclair, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 276 days.

(21) Appl. No.: 16/593,332

(22) Filed: Oct. 4, 2019

(65) Prior Publication Data

US 2020/0030550 A1    Jan. 30, 2020

Related U.S. Application Data

(63) Continuation of application No. 15/455,767, filed on Mar. 10, 2017, now Pat. No. 10,463,810, which is a
(Continued)

(51) Int. Cl.
*A61M 5/32* (2006.01)
*A61M 5/20* (2006.01)
(Continued)

(52) U.S. Cl.
CPC ........ *A61M 5/3293* (2013.01); *A61M 5/2066* (2013.01); *A61M 5/24* (2013.01);
(Continued)

(58) Field of Classification Search
CPC .......... A61M 5/2466; A61M 2005/247; A61M 2005/2474; A61M 5/288; A61M 5/3293; A61M 2005/31516
See application file for complete search history.

(56) References Cited

U.S. PATENT DOCUMENTS

| | | | |
|---|---|---|---|
| 1,715,771 A | 6/1929 | MacGregor |
| 1,798,142 A | 3/1931 | Cressler |

(Continued)

FOREIGN PATENT DOCUMENTS

| | | | |
|---|---|---|---|
| JP | 2007283132 A | 11/2007 |
| WO | 8800066 A1 | 1/1988 |

(Continued)

*Primary Examiner* — William R Carpenter
(74) *Attorney, Agent, or Firm* — The Webb Law Firm

(57) ABSTRACT

A drug delivery device is provided herein, the device including a reservoir for containing a medicament. The medicament includes a suspension of solids in a liquid carrier. The device also includes a needle having a distal end for injection into a patient, a proximal end in communication with the reservoir, and a lumen extending between the distal and proximal ends. A path is defined from the reservoir to the distal end of the needle through the lumen, the path having an inner diameter that decreases in a proximal to distal direction along at least a portion thereof. Advantageously, with the subject invention, a flow path may be defined which provides a more gradual transition in diameter from the reservoir to a distal tip of the needle. In this manner, changes in velocity of the suspension may be less abrupt than in the prior art, thus better maintaining solid particles in the suspension.

8 Claims, 4 Drawing Sheets

Related U.S. Application Data continuation of application No. 12/863,474, filed as application No. PCT/US2009/031448 on Jan. 20, 2009, now abandoned.

(60) Provisional application No. 61/011,409, filed on Jan. 17, 2008.

(51) Int. Cl.
  *A61M 5/24* (2006.01)
  *A61M 5/31* (2006.01)
  *A61M 5/315* (2006.01)

(52) U.S. Cl.
  CPC ........ *A61M 5/2448* (2013.01); *A61M 5/2466* (2013.01); *A61M 5/3134* (2013.01); *A61M 5/32* (2013.01); *A61M 2005/31516* (2013.01)

(56) References Cited

U.S. PATENT DOCUMENTS

| | | | |
|---|---|---|---|
| 2,217,602 A | 10/1940 | Smith | |
| 2,538,391 A * | 1/1951 | Smith | A61M 5/284 604/184 |
| 2,646,798 A | 7/1953 | Brown | |
| 4,553,962 A | 11/1985 | Brunet | |
| 4,968,302 A | 11/1990 | Schluter | |
| 5,116,319 A | 5/1992 | Van den Haak | |
| 5,263,934 A | 11/1993 | Haak | |
| 5,435,076 A * | 7/1995 | Hjertman | A61M 5/284 34/296 |
| 6,283,949 B1 | 9/2001 | Roorda | |
| 6,565,550 B1 | 5/2003 | Klein et al. | |
| 6,629,962 B2 | 10/2003 | Correa et al. | |
| 6,843,783 B2 * | 1/2005 | Ooyauchi | A61M 5/329 604/239 |
| 2004/0010235 A1 | 1/2004 | Weilbacher et al. | |
| 2004/0210196 A1 | 10/2004 | Bush Jr et al. | |
| 2011/0092917 A1 | 4/2011 | Wei et al. | |

FOREIGN PATENT DOCUMENTS

| | | |
|---|---|---|
| WO | 00678833 A1 | 11/2000 |
| WO | 02058769 A1 | 8/2002 |

* cited by examiner

DRUG DELIVERY DEVICE FOR DRUG SUSPENSIONS

The present application is a continuation of U.S. application Ser. No. 15/455,767, entitled "Drug Delivery Device for Drug Suspensions", filed Mar. 10, 2017, which is a continuation of U.S. application Ser. No. 12/863,474, entitled "Drug Delivery Device for Drug Suspensions", filed Jul. 19, 2010, which is a national phase entry application of International Application Serial No. PCT/US2009/031448, entitled "Drug Delivery Device for Drug Suspensions", filed Jan. 20, 2009, which claims priority to U.S. Provisional Patent Application Ser. No. 61/011,409, entitled "Minimizing Accumulation of Suspension Solids in a Drug Delivery System", filed Jan. 17, 2008, the entire disclosures of each of which are hereby incorporated by reference.

FIELD OF THE INVENTION

This invention relates to drug delivery devices for addressing the problems associated with solids coming out of drug suspension.

BACKGROUND OF THE INVENTION

Certain drugs or medicaments (those terms being used interchangeably herein) are preferably provided in powder or dry form (e.g., lyophilized form). Such powdered drugs are commonly suspended in a liquid diluent or carrier to allow delivery to an individual through injection. The powder drug is combined with the diluent prior to injection and administered in solution form. Drug delivery systems typically have a reservoir with a large diameter, for example a syringe barrel or drug cartridge, for containing the drug solution.

Prior art devices have been developed that provide a diluent and dry substance in separate chambers of a common container or reservoir, with the container being configured to permit the flow of the diluent to the dry substance to cause mixing thereof in forming a solution. For example, U.S. Pat. No. 4,874,381 to Vetter is directed to an injector configured for mixing, while U.S. Pat. No. 4,968,299 to Ahlstrand et al. is directed to a drug cartridge for mixing.

However, due to differences in density of solids and liquids in a solid/liquid suspension, the relative velocities of the two suspension constituents may be different, thus leading to possible separation of the solid particles out of solution. Drug delivery systems typically have a reservoir with a large diameter, for example a syringe barrel or drug cartridge, as compared to the fluid path used for delivery of the drug. The fluid path at delivery is reduced in diameter by travel of the solution through a hub or a needle. Due to abrupt changes to diameter in the fluid flow path, solid particles may come out of suspension.

SUMMARY OF THE INVENTION

A drug delivery device is provided herein, the device including a reservoir for containing a medicament. The medicament includes a suspension of solids in a liquid carrier. The device also includes a needle having a distal end for injection into a patient, a proximal end in communication with the reservoir, and a lumen extending between the distal and proximal ends. A path is defined from the reservoir to the distal end of the needle through the lumen, the path having an inner diameter that decreases in the proximal to distal direction along at least a portion thereof. Advantageously, with the subject invention, a flow path may be defined which provides a more gradual transition in diameter from the reservoir to the distal tip of a needle. In this manner, changes in velocity of the suspension may be less abrupt than in the prior art, thus better maintaining solid particles in the suspension.

These and other features of the invention will be better understood through a study of the following detailed description and accompanying drawings.

DETAILED DESCRIPTION OF THE INVENTION

Figure 1:
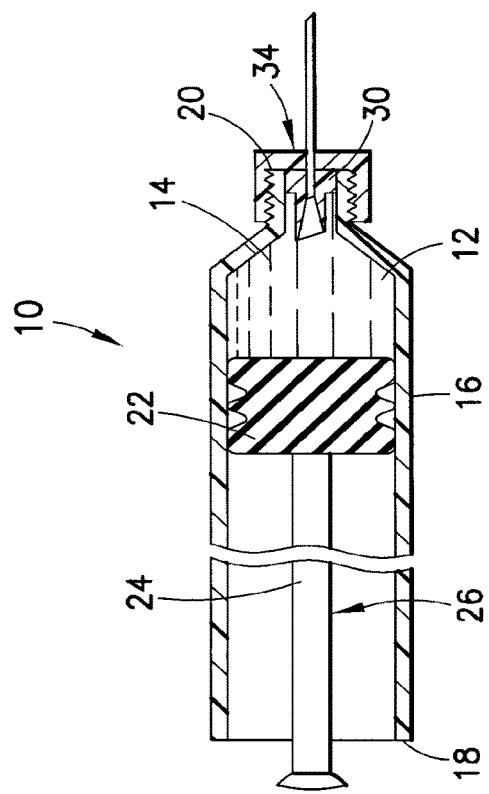
FIG. 1 is a schematic of a drug delivery device formed in accordance with the subject invention in the form of a syringe.
Figure 2:
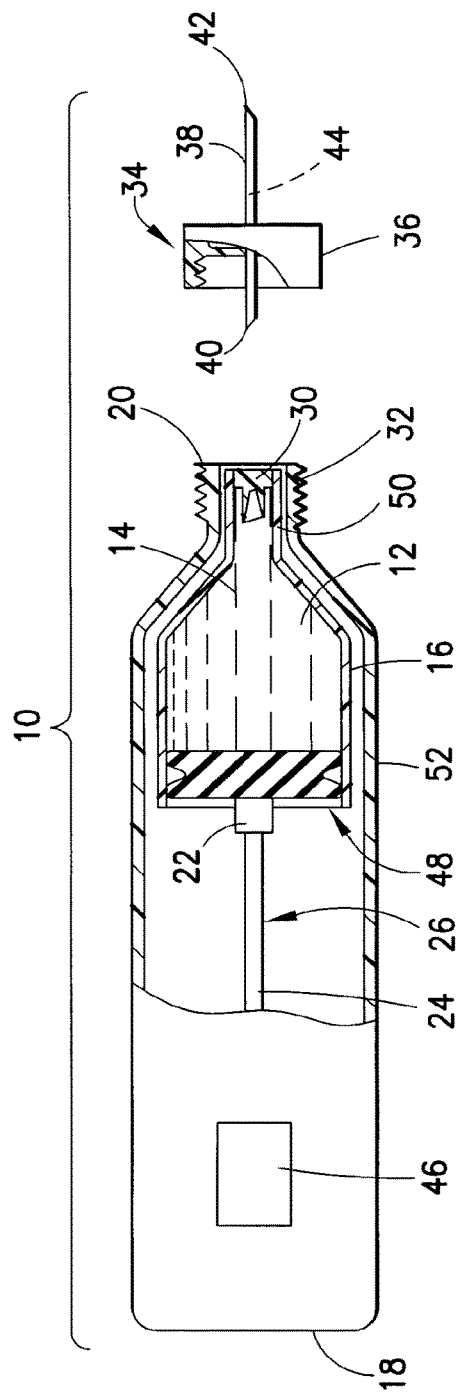
FIG. 2 is a schematic of a drug delivery device formed in accordance with the subject invention in the form of a pen injector; and, FIGS. 3-9 show various configurations of an inlet fluid port usable with the subject invention.

With reference to the figures, a drug delivery device 10 is shown for delivery of a drug in a fluid suspension to an individual. As will be appreciated by those skilled in the art, the drug delivery device 10 may be of various forms. With reference to FIGS. 1 and 2, the drug delivery device 10 may be in the form of a syringe (FIG. 1) or a pen injector or the like (FIG. 2). In any regard, the drug delivery device 10 includes a reservoir 12 in which a suspension 14 is maintained.

With reference to FIG. 1, the drug delivery device 10 includes a barrel 16. The barrel 16 includes a proximal end 18 and a distal end 20. As used herein, the term "proximal" shall refer to the end of the component further away from the injection site (i.e., the "non-patient end"), while the term "distal" shall refer to the end toward the injection site (i.e., the "patient end"). As known in the art, one or more stoppers 22 may be disposed in the barrel 16 in liquid-tight engagement therewith. A plunger rod 24 extends from the stopper 22 in a proximal direction, e.g., so as to be accessible at the proximal end 18 of the barrel 16. The stopper 22 and the plunger rod 24 together form a plunger 26 which is usable for urging the suspension 14 from the reservoir 12 as described below.

An opening 28 (FIG. 3) is defined in the distal end 20 of the barrel 16 which permits access to the reservoir 12. The opening 28 is sealed by a septum 30, which is preferably made of an elastomeric material, as is well known in the art. The barrel 16 may be formed with a reduced diameter adjacent to the distal end 20 so as to define a neck 32 onto which a pen needle assembly 34 may be mounted. The pen needle assembly 34 includes a hub 36 to which is mounted a needle cannula 38. The hub 36 is formed to mount onto the barrel 16, such as at the neck 32, through the use of cooperating mounting members, such as threads, or may be affixed thereto (such as by adhesive or fusion). The needle cannula 38 includes a proximal end 40, formed to extend into the reservoir 12 with the hub 36 being mounted to the barrel 16, and a distal end 42, formed for insertion into a patient. The needle cannula 38 extends through the septum 30 to access the reservoir 12. With mounting the pen needle assembly 34 onto the barrel 16, the needle cannula 38 pierces through the septum 30. A lumen 44 extends the length of the needle cannula 38 to communicate the proximal end 40 with the distal end 42.

As shown in FIG. 1, the reservoir 12 may be defined by a combination of various components, including the barrel 16, the stopper 22, and the septum 30. As is well known in the art, with the pen needle assembly 34 being mounted to the barrel 16, particularly with the proximal end 40 of the needle cannula 38 extending into the reservoir 12, distal advancement of the plunger 26 will cause the suspension 14 to be urged through the needle cannula 38.

With reference to FIG. 2, the drug delivery device 10 is shown in the form of a pen injector. The elements as discussed above with reference to FIG. 1 are similarly numbered. In the form of a pen injector, a dose-setting mechanism, schematically shown as a box 46, may be provided. Dose-setting mechanisms for pen injectors are well known in the prior art. In addition, in FIG. 1, the plunger 26 is shown to be of the manually driven type. In both variations of FIGS. 1 and 2, and in other possible configurations of the drug delivery device 10, the plunger 26 may be configured to be manually, semi-automatically, or automatically driven.

With a pen injector configuration, a drug cartridge 48 is typically provided. The drug cartridge 48 may include the barrel 16, the stopper 22 and the septum 30 and define the reservoir 12. The main difference between the drug cartridge 48 and the configuration of FIG. 1 is that the pen needle assembly 34 is mounted to neck 50 defined on outer barrel 52 of the drug delivery device 10, rather than being mounted to the barrel 16.

The suspension 14 includes a medicament for delivery into an individual. The suspension 14 includes solid components held in a liquid carrier. The active medicament agent or agents may be in the solid components of the suspension 14 and/or in the liquid carrier. The suspension 14 may contain solids dissolved to varying degrees, including at least some solids completely dissolved, or it may include solid particles, suspended in the liquid carrier. The suspension 14 may be pre-mixed before it is disposed in the reservoir 12, or it may be mixed after it has been disposed in the reservoir 12. For example, the reservoir 12 may house a liquid diluent and a solid drug in separate compartments, such as in a reconstitution arrangement as is known in the art, where the two components are mixed prior to delivery to an individual. Examples of suitable reconstitution arrangements may be found, for example, in U.S. Pat. No. 4,874,381 and in U.S. Pat. No. 4,968,299, the contents of which are incorporated by reference herein.

Figure 5:
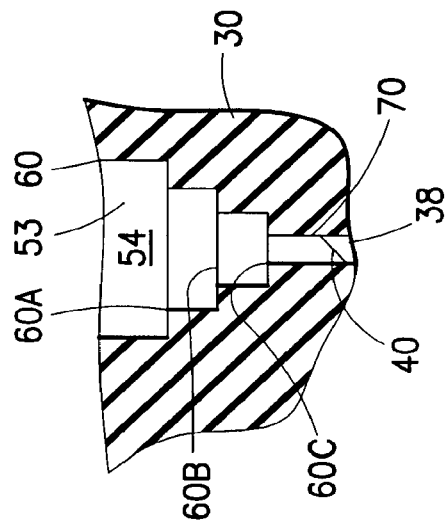

It is preferred that a fluid inlet port 53 be provided which is in communication, and contiguous contact, with the suspension 14 in the reservoir 12. The fluid inlet port 53 defines a flow control surface 54 which includes a proximal end 56 and a distal end 58, the proximal end 56 defining a larger diameter than the distal end 58. The proximal end 56 is located to be proximally of the proximal end 40 of the needle cannula 38. In addition, the proximal end 56 of the flow control surface 54 is configured to be larger than the lumen 44 of the needle cannula 38, particularly at the proximal end 40 thereof. The flow control surface 54 is generally tubular extending in a proximal to distal direction and formed with a converging shape going from the proximal end 56 to the distal end 58. The reduction in diameter may be gradual, such as being tapered, as shown in FIG. 3, or formed with one or more step changes, as shown in FIG. 5, or combinations thereof.

The suspension 14 flows through the flow control surface 54 and through the needle cannula 38 during administration. A flow path 60 for the suspension 14 is defined by at least the needle cannula 38, particularly the lumen 44, and the flow control surface 54. The flow path 60 is defined from the reservoir 12 to the distal end 42 of the needle cannula 38. With the flow control surface 54, at least a portion of the flow path 60 reduces in diameter as the suspension 14 flows in a distal direction. As shown in FIG. 3, the fluid path 60 is not defined by an immediate transition from the reservoir 12 to the needle cannula 38, thereby avoiding a significant drop in diameter. Rather, the flow control surface 54 provides a more gradual change in diameter which better avoids abrupt velocity changes in the suspension 14. With more gradual velocity changes, the suspension 14 may better maintain solid particles in solution.

Figure 4:
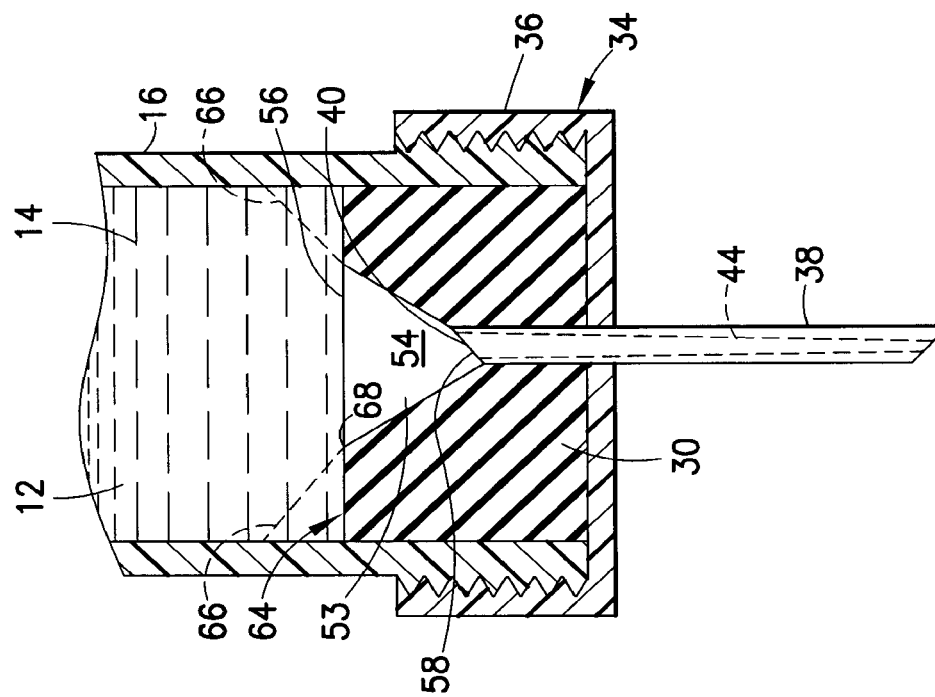
Figure 3:
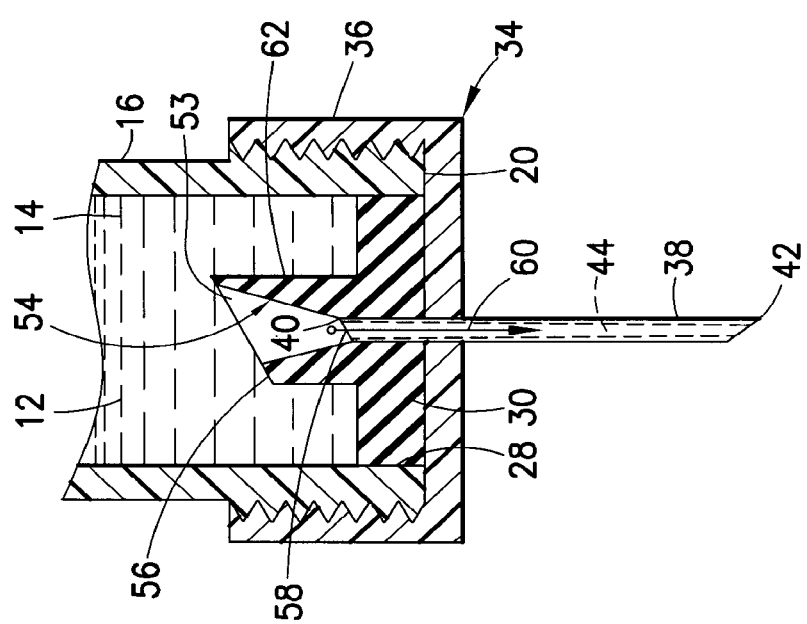

As shown in FIGS. 3 and 4, the fluid inlet port 53 may be defined by the septum 30. With reference to FIG. 3, a collar 62 may extend proximately from the septum 30 to define all or part of the fluid inlet port 53. Preferably, as shown in FIG. 4, the fluid inlet port 53 is defined within proximal face 64 of the septum 30. More preferably, portions of the proximal face 64 surrounding the fluid inlet port 53 may be angularly disposed to convergently guide the suspension 14 towards the flow control surface 54, as shown by the broken lines 66.

Edge 68, defined at the junction of the flow control surface 54 and the proximal face 64, may be rounded to further enhance the gradual change in velocity along the flow path 60. It is preferred that all transitions (corners, edges, changes in diameter) along the fluid path 60 be rounded to define arcuate or radiused transitions. For example, with reference to FIG. 5, edges 60A, 60B, and 60C, in addition to the edge 60, are preferably rounded.

As shown in FIGS. 3 and 4, it is preferred that the proximal end 40 of the needle cannula 38 coincide generally with the distal end 58 of the flow control surface 54, with the pen needle assembly 34 being mounted to the device 10. To ensure that the flow control surface 54 has sufficient length to communicate with the proximal end 40 of the needle cannula 38, the proximal end 40 may be configured to extend into the flow control surface 54, proximally of the distal end 58. Alternatively, as shown in FIG. 5, a channel 70 may extend distally from the distal end 58. The channel 70 may generally have the same diameter as the outer diameter of the needle cannula 38. The channel 70 may be configured such that the proximal end 40 is disposed therein during use. Flow then may pass from the flow control surface 54 to the needle cannula 38, via the channel 70. In this manner, the proximal end 40 of the needle cannula 38 is located distally of the distal end 58 of the fluid control surface 54.

With reference to FIG. 6, the needle cannula 38 may be directly fixed to the barrel 16, such as in a staked needle configuration. Here, the inlet flow port 53 may be defined directly by the barrel 16, particularly at the distal end 20 of the barrel 16. The distal end 20 of the barrel 16 may have a proximally-facing portion 72 located about the inlet flow port 53. Preferably, the flow control surface 54 extends distally from the proximally-facing portion 72. The proximally-facing portion 72 may be tapered and/or arcuately formed, particularly to convergently direct the suspension 14 to the inlet flow port 53. The inlet flow port 53 and the flow control surface 54 may be defined as described above.

During use, the suspension 14 is caused to be pressurized by the plunger 26 and urged distally. As the suspension 14 traverses the flow path 60, the suspension 14 will be urged along an increasing smaller flow path, particularly across the flow control surface 54. Even with the lumen 44 of the needle cannula 38 having a constant diameter, the flow control surface 54 allows for a gradual change in diameter.

In this manner, a more gradual change in velocity is achieved, particularly in transitioning from the reservoir 12 to the proximal end 40 of the needle cannula 38.

It is further possible to provide the lumen 44 of the needle cannula 38 with a change in diameter along the length thereof, particularly in a proximal to distal direction such that the lumen 44 at the proximal end 40 of the needle cannula 38 defines a larger diameter than at the distal end 42 of the needle cannula 38. For example, as shown schematically in FIG. 4, the lumen 44 may be at least partially tapered in a proximal to distal direction. Other changes in diameter of the lumen 44 are possible.

Figure 7:
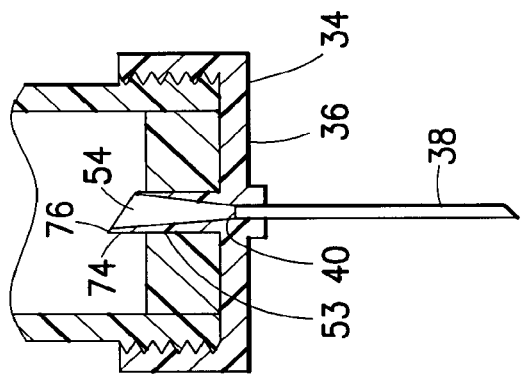
Figure 6:
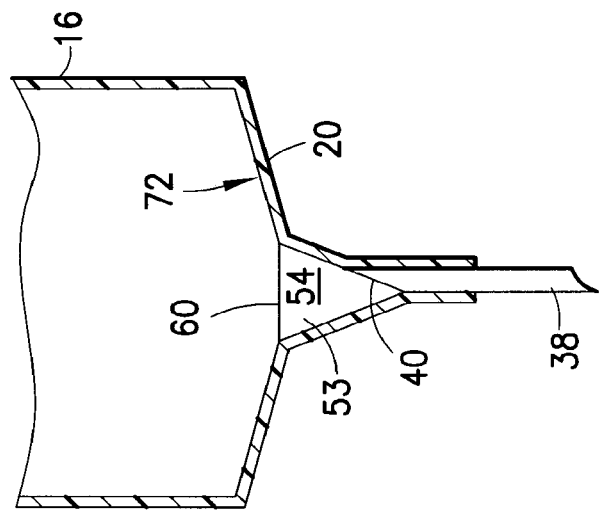
Figure 8:
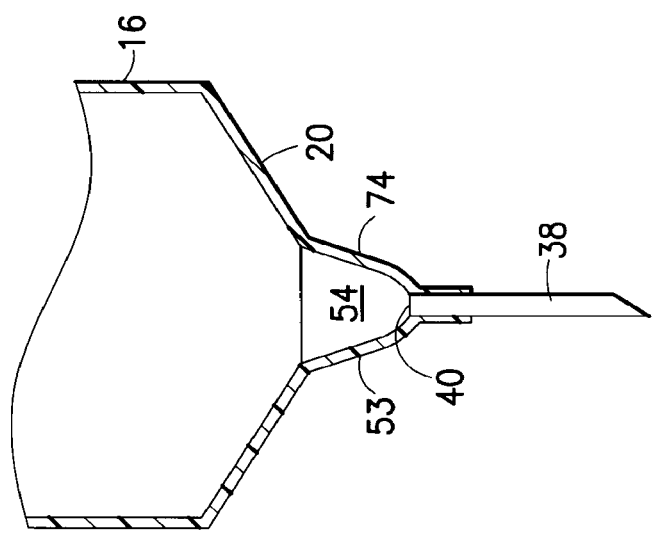

In addition to being formed by the septum 30 or by the barrel 16, the inlet flow port 53 may be defined by an ancillary or secondary component, such as by a sleeve 74. With respect to FIG. 7, the hub 36 may include the sleeve 74. In this arrangement, it is preferred that a proximal end 76 of the sleeve 74 be tapered or otherwise formed with a sharpened end such that with mounting of the hub 36 for use, the sleeve 74 may pierce through the septum 30. The inlet fluid port 53 may be defined by the sleeve 74 in similar fashion to that described above. In addition, the sleeve 74 may be mounted to the needle cannula 38 with or without being mounted to the hub 36. With reference to FIG. 8, the sleeve 74 may be provided as a separate component which is secured directly to the barrel 16 and the needle cannula 38, such as in a staked needle configuration. The barrel 16 may be configured as described above.

Figure 9:
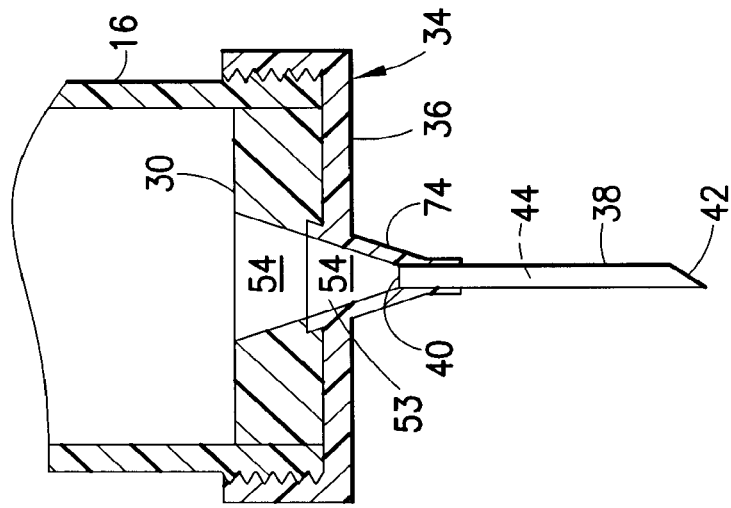

As will be appreciated by those skilled in the art, the various arrangements of the inlet fluid port 53 may be used in combination. For example, with reference to FIG. 9, the fluid inlet port 53 may be defined in the septum 30 and the sleeve 74 (the sleeve 74 being mounted to the hub 36 and/or the needle cannula 38). The flow control surfaces 54 both defined by the septum 30 and the sleeve 74 may collectively define the fluid path 60 so as to gradually reduce in diameter in a proximal to distal direction. In addition, as discussed above, the proximal face 64 of the septum 30 may be angled and/or the lumen 44 of the needle cannula 38 may be tapered. Various combinations of arrangements for generating reductions in the fluid path 60 may be utilized, particularly by the barrel 16, the septum 30, the sleeve 74, and/or the lumen 44, may be utilized.

What is claimed is:

1. A drug delivery device comprising:
   a reservoir configured to contain a medicament comprising a suspension of solids in a liquid carrier;
   an elastomeric septum sealing a distal end of said reservoir, said septum having a fluid inlet port;
   a hub mounted to said distal end of said reservoir, the hub defining a flow control surface configured to be in contiguous contact with the suspension; and
   a needle mounted to said hub, said needle having a distal end for injection into a patient, a proximal end in communication with said reservoir, and a lumen extending between said distal and proximal ends, a path being defined from said reservoir to said distal end of said needle through said lumen, wherein a proximal end face of the needle defines an opening that is tapered from a proximal end of the proximal end face of the needle to a distal end of the proximal end face of the needle such that an outer diameter of the proximal end face of the needle increases from the proximal end of the proximal end face of the needle to the distal end of the proximal end face of the needle,
   wherein said flow control surface has one or more step changes narrowing in a proximal-to-distal direction, and
   wherein said hub has a sleeve disposed within the fluid inlet port of the septum.

2. The drug delivery device of claim 1, wherein said flow control surface is defined within a proximal face of said septum.

3. The drug delivery device of claim 1, wherein at least a portion of a proximal face of said septum is angularly disposed to convergently guide said suspension towards said flow control surface.

4. The drug delivery device of claim 1, wherein an edge at a junction between a proximal face of said septum and said flow control surface is rounded.

5. The drug delivery device of claim 1, wherein said sleeve is tapered.

6. The drug delivery device of claim 1, wherein said sleeve has a sharpened proximal end that pierces through at least a portion of said septum when said hub is mounted to said reservoir.

7. The drug delivery device of claim 1, wherein transitions in diameter along said path are rounded.

8. The drug delivery device of claim 1, wherein an inner diameter of said path decreases in a proximal-to-distal direction with at least one step change in diameter.

* * * * *